United States Patent
Agazzi et al.

(10) Patent No.: US 12,097,329 B2
(45) Date of Patent: Sep. 24, 2024

(54) APPARATUS TO ADMINISTER DRUGS TO MECHANICALLY VENTILATED PATIENTS

(71) Applicant: Chiesi Farmaceutici S.p.A., Parma (IT)

(72) Inventors: Ruben Agazzi, Parma (IT); Benedetta Campolo, Parma (IT); Nicolò Dallacasa, Parma (IT); Edoardo Davico, Parma (IT); Chantal Erika Speziali, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 757 days.

(21) Appl. No.: 17/289,359

(22) PCT Filed: Oct. 22, 2019

(86) PCT No.: PCT/EP2019/078668
§ 371 (c)(1),
(2) Date: Apr. 28, 2021

(87) PCT Pub. No.: WO2020/088984
PCT Pub. Date: May 7, 2020

(65) Prior Publication Data
US 2021/0370007 A1    Dec. 2, 2021

(30) Foreign Application Priority Data
Oct. 30, 2018    (EP) ..................................... 18203344

(51) Int. Cl.
*A61M 16/08*    (2006.01)
*A61M 15/00*    (2006.01)
(Continued)

(52) U.S. Cl.
CPC .... *A61M 16/0816* (2013.01); *A61M 16/0883* (2014.02); *A61M 16/10* (2013.01);
(Continued)

(58) Field of Classification Search
CPC .. A61M 16/0057; A61M 16/04; A61M 16/08; A61M 16/0816; A61M 16/0833;
(Continued)

(56) References Cited

U.S. PATENT DOCUMENTS

| 2003/0005929 A1* | 1/2003 | Grychowski | A61M 15/0091 |
| | | | 128/203.12 |
| 2004/0173211 A1* | 9/2004 | Kladders | A61M 15/0048 |
| | | | 128/203.15 |

(Continued)

FOREIGN PATENT DOCUMENTS

| DE | 102008050218 A1 * | 7/2009 | ............ A61M 11/06 |
| EP | 1274406 B1 | 9/2006 | |

(Continued)

OTHER PUBLICATIONS

Machine translation of DE-102008050218-A1.*

(Continued)

*Primary Examiner* — Joseph D. Boecker
(74) *Attorney, Agent, or Firm* — Sterne, Kessler, Goldstein and Fox P.L.L.C.

(57) ABSTRACT

An apparatus to administer drugs to mechanically ventilated patients includes a mechanical ventilator, an artificial airway to be associated to a patient and a ventilation circuit connecting the mechanical ventilator to the artificial airway. The ventilation circuit includes: an inspiratory line, a dry powder inhaler disposed in line on the inspiratory line and a connector operatively connected to the dry powder inhaler and to the inspiratory line. The connector includes: a first duct facing an outlet port of the dry powder inhaler and connected or configured to be connected to a tube section of the inspiratory line placed downstream the dry powder inhaler; a second duct facing an air inlet port of the dry powder inhaler and connected or configured to be connected to a (Continued)

tube section of the inspiratory line placed upstream the dry powder inhaler.

14 Claims, 5 Drawing Sheets

(51) Int. Cl.
    *A61M 16/00*     (2006.01)
    *A61M 16/04*     (2006.01)
    *A61M 16/10*     (2006.01)
    *A61M 16/20*     (2006.01)

(52) U.S. Cl.
    CPC ..... *A61M 15/0091* (2013.01); *A61M 16/0057* (2013.01); *A61M 16/04* (2013.01); *A61M 16/0833* (2014.02); *A61M 16/204* (2014.02); *A61M 2202/064* (2013.01)

(58) Field of Classification Search
    CPC .. A61M 16/0883; A61M 16/10; A61M 15/00; A61M 15/0091; A61M 2202/064
    See application file for complete search history.

(56) References Cited

U.S. PATENT DOCUMENTS

| | | | |
|---|---|---|---|
| 2006/0251586 A1* | 11/2006 | Zierenberg | A61M 15/0045 128/200.23 |
| 2008/0000470 A1* | 1/2008 | Minocchieri | A61M 16/0003 128/200.21 |
| 2008/0017198 A1 | 1/2008 | Ivri | |
| 2009/0025722 A1* | 1/2009 | Pieper | A61M 16/08 128/203.15 |
| 2011/0146670 A1* | 6/2011 | Gallem | A61M 11/005 128/200.14 |
| 2012/0138049 A1 | 6/2012 | Wachtel | |
| 2013/0319410 A1* | 12/2013 | Berkland | A61M 16/0463 128/203.15 |
| 2016/0339198 A1* | 11/2016 | Fraser | A61M 16/0048 |
| 2020/0139058 A1* | 5/2020 | Longest | A61M 16/14 |
| 2021/0275760 A1* | 9/2021 | Hunter | A61M 11/003 |

FOREIGN PATENT DOCUMENTS

| | | |
|---|---|---|
| WO | 2001078693 A2 | 10/2001 |
| WO | 2001078695 A3 | 10/2001 |
| WO | 2004012801 A1 | 2/2004 |
| WO | 2013037809 A1 | 3/2013 |
| WO | 2013110632 A1 | 8/2013 |
| WO | 2014095700 A1 | 6/2014 |
| WO | 2015085362 A1 | 6/2015 |
| WO | 2015091685 A1 | 6/2015 |
| WO | 2016000983 A1 | 1/2016 |

OTHER PUBLICATIONS

A novel in-line delivery system to administer dry powder mannitol to mechanically ventilated patients—Journal of aerosol medicine and pulmonary delivery—vol. 30, No. 2, 2017—Mary Ann Liebert Inc.—pp. 100-107.

International Search Report in PCT/EP2019/078668, mailed Dec. 20, 2019, 3 pages.

* cited by examiner

APPARATUS TO ADMINISTER DRUGS TO MECHANICALLY VENTILATED PATIENTS

BACKGROUND OF THE INVENTION

The present invention relates to an apparatus to administer drugs to mechanically ventilated patients. In particular, the present invention relates to a ventilation apparatus for mechanically ventilation of patients including a dry powder inhaler to administer powder drug/medicament preparation to mechanically ventilated patients.

Every day, many patients affected by severe forms of respiratory diseases, such as asthma and chronic obstructive pulmonary disease, are admitted to hospitals requiring mechanical ventilation. Most of the ambulatory patients receive drugs, in particular bronchodilators such as $beta_2$-adrenergic agonists and anticholinergics, by inhalation. In said kind of patients, so far, the major aerosol-generating devices that have been employed include pressurized metered-dose inhalers (pMDIs), and nebulizers. While it is also feasible to employ dry powder inhalers (DPIs) during mechanical ventilation, their efficacy has not fully been demonstrated yet. This could in part be due to the poor efficiency of drug delivery by this route in its setting. Furthermore, the treatment of patients affected by severe respiratory diseases would benefit by the use DPIs able of delivering a significant fraction of drug particles reaching the distal part of the lung tree. Said fraction of particles has been quoted in the art as extra-fine.

A multi-dose dry powder inhaler, able of delivering extra-fine particles, is known from WO 2004/012801 by the applicant of this application. This powder inhaler comprises a container for storing a powdered medicament, a metering member having a dosing recess to be filled with a dose of the powdered medicament, and a mouthpiece being in communication with an inhalation channel of the powder inhaler. Furthermore, the powder inhaler comprises a protective member which is slidingly moveable on the metering member between a closed position, in which it at least covers the dosing recess of the metering member if the metering member is in an inhalation position, and an open position, in which it exposes the dosing recess thereby enabling inhalation of the dose of the powdered medicament contained in the dosing recess. The protective member is coupled to an inhalation actuated mechanism in such a manner that the inhalation actuated mechanism moves the protective member from its closed position to its open position only if there is an inhalation suction force exerted by a user which exceeds a predetermined level.

A flap for an inhalation actuated mechanism of the aforementioned powder inhaler is known from WO 2016/000983 by the applicant of this application. The flap comprises a base member, a skirt structure projecting from a surface of the base member, and a coupling portion to be coupled to a resilient member of the inhalation actuated mechanism.

Therefore, it would be advantageous to provide an apparatus for improving the efficiency of drug delivery to mechanically ventilated patients by DPIs such as those disclosed in WO 2004/012801 and WO 2016/000983.

In the prior art, a system to administer a powder medicament preparation to a mechanically ventilated patient without disconnection from a ventilator is disclosed in paper "*A novel in-line delivery system to administer dry powder mannitol to mechanically ventilated patients—Journal of aerosol medicine and pulmonary delivery—Volume* 30*, Number* 2*,* 2017—Mary Ann Liebert Inc. —Pp. 100-107".

This paper discloses to split the inspiratory line from a ventilator into two parallel lines where one contains a humidifier for normal breathing cycle and the other line contains a single dose dry powder inhaler (Osmohaler®). Osmohaler® operates on a piercing mechanism, which pierces two holes, one at each end of the capsule, through which the powder will exit as the capsule spins resulting from the air entrained into the inhaler during inspiration. The inspiratory air goes through the dry powder line and aerosolizes the mannitol powder only when its administration to a patient is required.

US2012/0138049 relates to an adapter and inhalation device. A connector for connecting to an atomizer and one patient-side connection is provided on the adapter, fluidically connected to each other in an unbranched manner. The inhalation device comprises a chamber for intermediately storing an aerosol. A connection for the atomizer, a patient-side connection, and a third connection for breathable air are provided on the inhalation device. The chamber is connected to the atomizer and is connected to the connection for breathable air on the inlet side, so that breathable air can flow from the breathable air connection into the chamber.

BRIEF SUMMARY OF THE INVENTION

It is an object of the present invention to improve efficacy of administration of powder drug/medicament preparations to mechanically ventilated patients.

In particular, it is an object of the present invention to increase the fraction of particles of the dose able to reach the respiratory tract in the patient upon administration by dry powder inhalers.

It is a further object of the present invention to provide an apparatus to administer powder drug/medicament preparation to mechanically ventilated patients which is easy to use and safe for professional caregivers.

It is an object of the present invention to make it feasible to administer the drug powder during the inspiratory act and over a short period of time (optionally less than 1 min) without disconnecting or interrupting the mechanical ventilation.

It is a further object of the present invention to allow connection of a dry powder inhaler to a mechanical ventilator with standard ventilation tubing systems.

At least one of the above objects is substantially achieved by an apparatus to administer drugs to mechanically ventilated patients according to one or more of the appended claims.

Aspects of the invention are disclosed in the following.

In accordance with a $1^{st}$ independent aspect, an apparatus to administer drugs to mechanically ventilated patients, comprises:
  a mechanical ventilator;
  an artificial airway to be associated to a patient;
  a ventilation circuit connecting the mechanical ventilator to the artificial airway;
  wherein the ventilation circuit comprises:
  an inspiratory line;
  a dry powder inhaler disposed in line on the inspiratory line;
  a connector operatively connected to the dry powder inhaler and to the inspiratory line;
  wherein the connector comprises:
  a first duct facing an outlet port of the dry powder inhaler and connected or configured to be connected to a tube section of the inspiratory line placed downstream the dry powder inhaler;

a second duct facing an air inlet port of the dry powder inhaler and connected or configured to be connected to a tube section of the inspiratory line placed upstream the dry powder inhaler.

In accordance with a 2$^{nd}$ independent aspect, a connector configured to be connected to a dry powder inhaler and to an inspiratory line of a ventilation circuit of a ventilation apparatus, comprises:
 a first duct facing an outlet port of the dry powder inhaler and connected or configured to be connected to a tube section of the inspiratory line placed downstream the dry powder inhaler;
 a second duct facing an air inlet port of the dry powder inhaler and connected or configured to be connected to a tube section of the inspiratory line placed upstream the dry powder inhaler.

In accordance with a 3$^{rd}$ independent aspect, a method for ventilating a patient comprises:
 associating an artificial airway to a patient;
 connecting a ventilation circuit to the artificial airway and to a mechanical ventilator;
 disposing a dry powder inhaler in line on an inspiratory line of the ventilation circuit;
 wherein disposing the dry powder inhaler comprises:
 connecting a first duct of a connector to a tube section of the inspiratory line placed downstream the dry powder inhaler, wherein said first duct faces an outlet port of the dry powder inhaler; and
 connecting a second duct of the connector to a tube section of the inspiratory line placed upstream the dry powder inhaler, wherein said second duct faces an air inlet port of the dry powder inhaler.

In a 4$^{th}$ aspect, a kit or assembly comprises a dry powder inhaler and a connector according to the 2$^{nd}$ aspect and/or according to one of the following aspects.

In an aspect, the dry powder inhaler is a medium-high resistance dry powder inhaler.

In an aspect, a required inspiratory flow rate of the dry powder inhaler is about 50-60 l/min.

In an aspect, the dry powder inhaler is a single dose or a multi-dose dry powder inhaler, optionally either with pre-subdivided single doses or pre-loaded with a quantity of powdered drug/medicament sufficient for multiple doses, each dose being created by a metering member within the inhaler.

Preferably, the dry powder inhaler is a medium-high resistance multi-dose dry powder inhaler.

In an aspect, the dry powder inhaler comprises a container for storing a powdered drug/medicament (optionally configured to store a single dose or pre-subdivided single doses or a quantity of powdered drug/medicament sufficient for multiple doses).

In an aspect, at least in a working position, the powdered drug/medicament is in fluid communication with the air inlet port and with the outlet port for enabling flowing of air through the inhaler from the air inlet port to the outlet port and inhalation of a dose of the powdered drug/medicament.

In an aspect, the dry powder inhaler comprises:
 a container for storing a powdered drug/medicament;
 a metering member having a dosing recess, the metering member being moveable between a filling position, in which the dosing recess is in alignment with an opening of the container so as to be filled with a dose of the powdered drug/medicament, and an inhalation position, in which the dosing recess is in alignment with an inhalation channel;
 wherein the outlet port is in communication with the inhalation channel for enabling inhalation of the dose of the powdered drug/medicament contained in the dosing recess of the metering member when the metering member is in the inhalation position.

In an aspect, the dry powder inhaler comprises an inhalation or breath actuated mechanism which is coupled to a protective member for the dosing recess of the metering member such that, if the protective member is in a closed position in which it at least partly covers the dosing recess, the inhalation actuated mechanism causes the protective member to move to an open position, in which the protective member does not cover the dosing recess, if an inhalation suction force on the inhalation channel exceeds a predetermined value.

In an aspect, the inhalation actuated mechanism comprises a flap.

In an aspect, the flap is arranged such that it is pivotable between a first position and a second position, wherein the flap is coupled to the protective member such that, if there is an inhalation suction force exceeding the predetermined value, the flap is moved from the first position to the second position, thereby causing the protective member to move from the closed position to the open position.

In an aspect, a resilient member is arranged such that it holds the flap in its first position if the resilient member is discharged, while the resilient member releases the flap if the resilient member is tensioned, so as to allow the flap to be moved from its first position to its second position by the inhalation suction force exceeding the predetermined value.

In an aspect, the flap comprises a base member with a substantially plate-shaped flat portion from which a skirt or frame structure projects upward, wherein the skirt extends along a periphery of the base portion and is open toward the front.

In an aspect, the outlet port and the air inlet port of the dry powder inhaler are placed on a same side of said dry powder inhaler.

In an aspect, the dry powder inhaler comprises a casing having an upper part provided with the outlet port and the air inlet port.

In an aspect, the casing comprises a mouthpiece delimiting the outlet port and presents an aperture, optionally at least one slot, defining the air inlet port.

In an aspect, the first duct is straight.

In an aspect, the second duct is curved, optionally U-shaped.

In an aspect, the connector comprises a connector body.

In an aspect, the first duct and the second duct of the connector present respectively a first opening and a second opening placed side by side on the connector body.

In an aspect, the connector comprises a curved tube connected to the connector body, wherein said curved tube delimits at least in part the second duct; wherein the second opening is placed at a proximal end of the curved tube.

In an aspect, the connector comprises a straight tube section protruding from the connector body, wherein said straight tube section delimits at least in part the first duct; wherein the first opening is placed at a proximal end of the straight tube section.

In an aspect, the proximal end of the curved tube is substantially parallel to the first duct and/or to the straight tube section.

In an aspect, the curved tube presents a terminal end substantially parallel to the first duct.

In an aspect, the curved tube and/or second duct is bent backwards with respect to the straight tube section and/or first duct.

In an aspect, the curved tube is in part placed at a side of the dry powder inhaler, optionally wherein the terminal end of the curved tube is placed at a side of the dry powder inhaler.

In an aspect, the curved tube is U-shaped.

In a further aspect, the connector is made of a single piece optionally of molded plastic.

In an aspect, a curvature radius of the curved tube is between 14 mm and 16 mm, optionally of 15 mm, wherein the curvature radius is the curvature radius of a mid-line of the curved tube.

In an aspect, the first duct inside the straight tube section presents a diameter between 20 mm and 24 mm, optionally between 21 mm and 23 mm.

In an aspect, the second duct inside the curved tube presents a passage section between 120 mm$^2$ and 130 mm$^2$, optionally between 125 mm$^2$ and 128 mm$^2$.

In an aspect, the first duct inside the straight tube section has a conical shape. In an aspect, a terminal end of the second duct has a conical shape.

In an aspect, the first duct and/or the terminal end of the second duct has/have a male/female coupling with tube sections/s of the ventilation circuit.

In an aspect, the first duct and/or the terminal end of the second duct are manufactured according to ISO 5356-1: 2004 specifying dimensional and gauging requirements for cones and sockets intended for connecting anaesthetic and respiratory equipment, e.g. in breathing systems, anaesthetic-gas scavenging systems and vaporizers. ISO 5356-1: 2004 gives requirements for the following conical connectors: 8.5 mm sizes intended for use in paediatric breathing systems: 15 mm and 22 mm sizes intended for general use in breathing systems.

In an aspect, the connector is detachably connected to the dry powder inhaler, wherein optionally the connector is snap-fitted on the dry powder inhaler or the connector is inserted/slipped on the on the dry powder inhaler.

In an aspect, disposing the dry powder inhaler comprises connecting the connector to the dry powder inhaler.

In an aspect, the connector has a connection seat counter-shaped to a side of the dry powder inhaler exhibiting the outlet port and the air inlet port.

In an aspect, the connector body has a connection seat counter-shaped to a side of the dry powder inhaler exhibiting the outlet port and the air inlet port.

In an aspect, the connection seat presents a recess for a mouthpiece of the dry powder inhaler.

In an aspect, the dry powder inhaler comprises a cover or lid, optionally hinged to the casing.

In an aspect, the first opening and the second opening open in said connection seat.

In an aspect, the cover or lid is movable between a first closed configuration, in which said cover is positioned on the outlet port and on the air inlet port, and an open configuration, in which said cover is spaced from the outlet port and the air inlet port to allow connection to the connector.

In an aspect, the cover or lid is rotated between the first and second configuration.

In an aspect, the connection seat is fashioned in a first face of the connector body.

In an aspect, the straight tube section and the curved tube protrude from a second face of the connector body opposite the first face.

In an aspect, the inspiratory line comprises a main branch and an auxiliary branch disposed in parallel.

In an aspect, a T or Y junction splits the inspiratory line coming from the mechanical ventilator into said main branch and said auxiliary branch.

In an aspect, the dry powder inhaler is placed in line on the auxiliary branch.

In an aspect, the ventilation circuit may comprise at least one valve disposed upstream the dry powder inhaler to selectively direct ventilation air through the main branch or through the auxiliary branch.

In an aspect, when said at least one valve is configured to direct ventilation air through the auxiliary branch, pressure of ventilation air triggers the dry powder inhaler to deliver a dose.

In an aspect, pressure of ventilation air triggers the dry powder inhaler to deliver a dose during inspiration cycle performed by the mechanical ventilator.

In an aspect, the method comprises: performing mechanical ventilation and delivering a dose from the dry powder inhaler while performing mechanical ventilation.

In an aspect, delivering a dose is performed by actuating said at least one valve to direct ventilation air through the auxiliary branch.

In an aspect, delivering a dose is performed by actuating said at least one valve to divert ventilation air from the main branch to the auxiliary branch.

In an aspect, the ventilation circuit comprises at least one non-return/one-way valve disposed downstream the dry powder inhaler to prevent air from flowing back into the dry powder inhaler.

In an aspect, the ventilation circuit comprises a filter in line on the auxiliary branch and upstream the dry powder inhaler.

In an aspect, the ventilation circuit further comprises an expiratory line connecting the artificial airway to the mechanical ventilator.

In an aspect, the powdered medicament filled in the inhaler is under the form of powder formulation comprising coarse carrier particles of a physiologically acceptable excipient, and micronized particles of one or more active ingredients currently utilized by inhalation.

Advantageously, the coarse carrier particles may have a mass median diameter (MMD) higher than 90 micron, and preferably the mass diameter (MD) is comprised between 50 micron and 500 micron, more preferably between 150 and 400 micron, even more preferably between 210 and 355 micron. The coarse carrier particles have preferably a relatively highly fissured surface, that is, on which there are clefts and valleys and other recessed regions, referred to herein collectively as fissures. The "relatively highly fissured" surface of the coarse carrier particles may be defined in terms of fissure index or rugosity coefficients as disclosed in WO 01/78695 and WO 01/78693 and they can be characterized according to the description therein reported.

Preferably, said powder formulation may further comprises a fraction of micro-particles having a MMD lower than 35 micron composed of particles of a physiologically acceptable excipient and an additive material selected from the class of the anti-adherents such as the amino acids leucine and isoleucine or of the lubricants such as magnesium stearate; sodium stearyl fumarate stearyl alcohol, stearic acid and sucrose mono-palmitate.

More preferably said powder formulation comprises a fraction of micro-particles having a MMD lower than 15 micron, preferably lower than 10 micron, composed of particles of a physiologically acceptable excipient and particles of magnesium stearate according to the teaching of EP 1274406.

The physiologically acceptable excipient may be constituted of any amorphous or crystalline physiologically acceptable inert material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate. Examples of commercial lactose are Capsulac® and Pharmatose®. An example of commercial mannitol is Pearlitol®. In a preferred embodiment, the fraction of micro-particles is composed of 98% by weight of α-lactose monohydrate and 2% by weight of magnesium stearate and the ratio between the fraction of micro-particles and the fraction of coarse particles made of α-lactose monohydrate particles is 10:90% by weight, respectively.

The amount of magnesium stearate in the final formulation is advantageously comprised between 0.02% and 1.0% by weight, preferably between 0.05 and 0.5% by weight, more preferably between 0.1 and 0.4% by weight on the total weight of the formulation.

The active ingredient may be practically any pharmaceutically drug which can be administered by inhalation as dry powder.

Advantageously, the drugs are used for the treatment of respiratory diseases such as asthma, chronic obstructive pulmonary disease (COPD), pulmonary hypertension, idiopathic pulmonary fibrosis and cystic fibrosis.

As an example, they may be chosen from short-acting and long-acting beta$_2$-agonists such as terbutalin, reproterol, salbutamol, salmeterol, formoterol, milveterol, indacaterol, olodaterol, fenoterol, clenbuterol, bambuterol, broxaterol, epinephrine, isoprenaline or hexoprenaline or salts and/or solvate forms thereof; short-acting and long-acting anticholinergics such as tiotropium, ipratropium, oxitropium, oxybutynin, aclidinium, trospium, or other compounds known with the codes GSK 573719 and GSK 1160274, in form of salts and/or solvate forms thereof; bifunctional Muscarinic Antagonist-beta2 Agonist (MABA) such as GSK 961081; corticosteroids such as butixocart, rofleponide, flunisolide, budesonide, ciclesonide, mometasone and its ester, i.e. furoate, fluticasone and its ester, i.e. propionate and furoate, beclomethasone and its ester, i.e. propionate, loteprednol or triamcinolone acetonide and solvate forms thereof; phosphodiesterase-inhibitors such as filaminast, piclamilast or roflumilast, human neutrophil elastase (HNE) inhibitors such as those disclosed in WO 2013/037809 and WO 2014/095700; and phosphoinositide 3-kinases inhibitors such as those disclosed in WO 2015/091685.

Other drugs which could advantageously be used are beta-adrenergic agonists such as adrenaline and nor-adrenaline, hormones such as insulin, antibiotics such as tobramycin and colistin, and mannitol.

Powder formulations comprising a beta$_2$-agonist and/or an anti-cholinergic, and/or a corticosteroid for inhalation, alone or in any combination thereof, constitute particular embodiments of the invention.

An even more preferred embodiment of the invention concerns formulations comprising formoterol fumarate dihydrate and beclometasone dipropionate, and optionally glycopyrronium bromide.

Applicant verified that the apparatus, method and assembly according to the present invention allow to administer powder drug/medicament preparations to any ventilated patient (while performing ventilation) with high efficiency and effectiveness and without disconnecting or interrupting the mechanical ventilation and to exclude the dry powder inhaler from the ventilation circuit when drug administration is not required.

Ventilated patients who may benefit of the apparatus of the invention are those, of any sex and/or age, affected by severe, acute or chronic, controlled or uncontrolled, forms of inflammatory or obstructive respiratory disease such as asthma and chronic obstructive pulmonary disease (COPD), in particular the ones hospitalized for a COPD exacerbation.

The patient who may preferably benefit of the apparatus of the invention are those affected by severe persistent asthma, as defined in the Global INitiative for Asthma (GINA) guidelines, or affected by severe COPD as defined is the Global initiative for chronic Obstructive Pulmonary Disease (GOLD) guidelines. The apparatus, method and assembly according to the present invention allow to deliver to the patient an extra-fine fraction equal to or higher than 20% of nominal dose of the drug/medicament powder upon administration by a multi-dose powder inhaler. Indeed, when the dry powder inhaler is actuated by the pressure generated by the mechanical ventilator, air flows through a flow path delimited by the air inlet port, the dosing recess, the inhalation channel and the outlet port and a dose of the powdered drug/medicament is de-agglomerated and delivered.

Applicant verified that the connector according to the invention allows to place the dry powder inhaler in the most proximal position respect to the artificial airway in order to short the travel of the drug powder to the patient, to limit powder deposition in the conduits.

Applicant also verified that the connector according to the invention allows to place the dry powder inhaler in the most proximal position respect to inspiratory limb of the mechanical ventilator in order to avoid pressure losses upstream the inhaler.

Applicant also verified that such position, together with the fluid dynamics features of the connector, makes the dry powder inhaler mechanism be activated only by the positive ventilator airflow (inspiratory act), even if the dry powder inhaler is a medium-high resistance multi-dose dry powder inhaler.

Applicant also verified that the activation of the dry powder inhaler is rapid and enhances powder aerosolization (it promotes the disaggregation of the drug product and enhances the cut off of the coarse fraction before the drug product enters the patient's upper airways).

Applicant also verified that the apparatus, method and assembly according to the present invention allow not to increase the length and dead spaces of the tubing system, limiting the tubing system fluid resistance and limiting transient contact of the drug powder with the humidified air.

Furthermore, the filter in line on the auxiliary branch and upstream the dry powder inhaler allows to dry the air flow before it comes in contact with the drug product and the one way valve limits contamination by the patient exhaled air and avoids drug powder escape from the circuit.

Applicant also verified that the apparatus according to the present invention allow connection of a dry powder inhaler to a mechanical ventilator with standard ventilation tubing systems and is easy to use and safe for professional caregivers.

Definitions

As used herein, the term "dry powder inhaler (DPI)" refers to a device that delivers medication to the lungs in the form of a dry powder. DPIs can be divided into two basic types:

i) single dose inhalers, for the administration of pre-subdivided single doses of the active compound;

ii) multi-dose dry powder inhalers (MDPIs), either with pre-subdivided single doses or pre-loaded with quantities of active ingredient sufficient for multiple doses; each dose is created by a metering unit within the inhaler.

On the basis of the required inspiratory flow rates (l/min) which in turn are strictly depending on their design and mechanical features, DPI's are also divided in:

i) low-resistance devices (>90 l/min);
ii) medium-resistance devices (about 60-90 l/min);
iii) medium-high resistance devices (about 50-60 l/min);
iv) high-resistance devices (less than 30 l/min).

The reported classification is generated with respect to the flow rates required to produce a pressure drop of 4 KPa (KiloPascal) in accordance to the European Pharmacopoeia (Eur Ph).

A "mechanical ventilator" is a medical device, a machine designed to move breathable air into and out of the lungs, to provide breathing for a patient who is physically unable to breathe, or breathing insufficiently. Modern ventilators are computerized machines. Ventilators are chiefly used in intensive care medicine, home care, and emergency medicine (as standalone units) and in anesthesia (as a component of an anesthesia machine).

The terms "upstream" and "downstream" may be used with reference to the relative positions taken by components belonging to or operating on the ventilation apparatus. These terms are to be understood with reference to an air/fluid flow direction from the ventilator to the patient P in an inspiratory line and from the patient P to the ventilator in an expiratory line.

DETAILED DESCRIPTION

Figure 1:
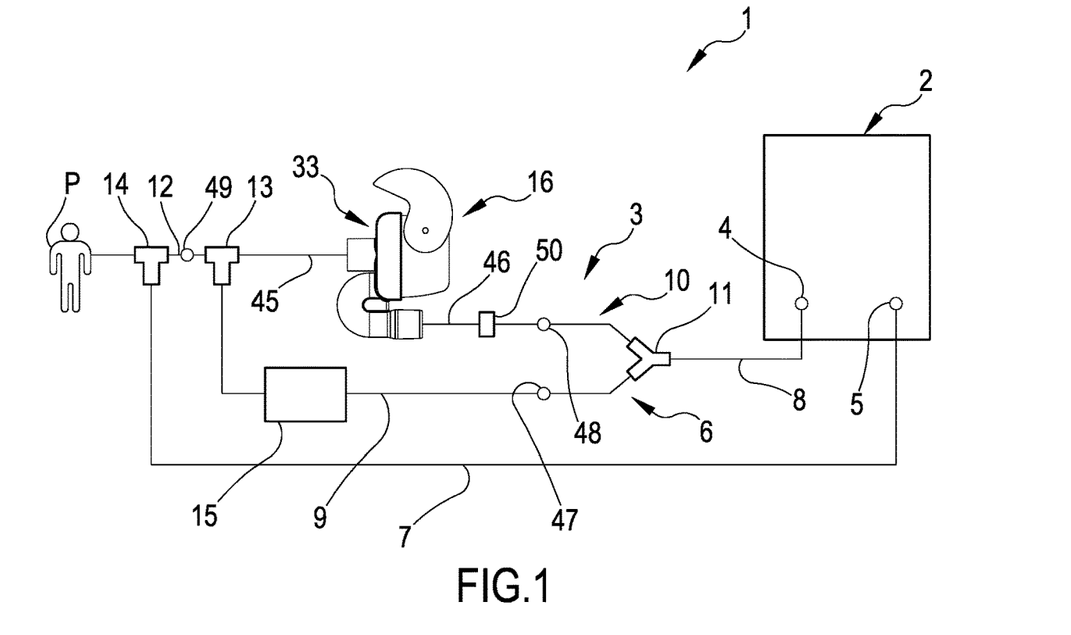
FIG. 1 shows a schematic representation of an apparatus to administer drugs to mechanically ventilated patients according to the present invention.

With reference to the appended drawings, FIG. 1 shows a schematic representation of an apparatus 1 to administer drugs to mechanically ventilated patients according to the present invention. The apparatus of the invention comprises a ventilation apparatus and a dry powder inhaler as will be detailed in the following description. Apparatus 1 comprises a mechanical ventilator 2 and an artificial airway, not shown, configured for association to a patient P, and a ventilation circuit 3 connecting the mechanical ventilator 2 to the artificial airway. The mechanical ventilator 2 may be known per se and may comprise a pneumatic system electrically powered by a power unit and controlled by an electronical control unit. In the illustrated embodiment, the mechanical ventilator 2 presents an inspiratory connection 4 and an expiratory connection 5. The artificial airway may be a facial mask, a tracheal tube, a supraglottic airway, a cricothyrotomy or tracheostomy tube.

The ventilation circuit 3 comprises an inspiratory line 6 and an expiratory line 7. The inspiratory line 6 puts in fluid communication the artificial airway and the patient P with the inspiratory connection 4 of the mechanical ventilator 2. The expiratory line 7 puts in fluid communication the artificial airway and the patient P with the expiratory connection 5 of the mechanical ventilator 2.

The inspiratory line 6 comprises a first branch 8 connected to the inspiratory connection 4. The first branch 8 splits into a main branch 9 and an auxiliary branch 10 disposed in parallel one with respect to the other. A first junction 11, e.g. shaped like a T or a Y, is placed at an end of the first branch 8 to connect said first branch 8 to the main and auxiliary branches 9, 10. The main branch 9 and the auxiliary branch 10 merge one into the other and into a second branch 12 close to the artificial airway. A second junction 13, i.e. shaped like a T or a Y, is placed at an end of the second branch 12 to connect the main and auxiliary branches 9, 10 to said second branch 12.

The expiratory line 7 may be a single tube and is connected to the artificial airway between the patient P and the second junction 13. A third junction 14, i.e. shaped like a T or a Y, connects the artificial airway to the second branch 12 and to the expiratory line 7.

A humidifier 15 is placed on the main branch 9. A dry powder inhaler (DPI) 16 is disposed in line on the auxiliary branch 10.

The dry powder inhaler 16 shown in the attached figures is a medium-high resistance (a required inspiratory flow rate of the dry powder inhaler is about 50-60 l/min), and multi-dose dry powder inhaler. The dry powder inhaler 16 may be the one known from WO 2004/012801 or from WO 2016/000983 by the applicant of this application.

Figure 10:
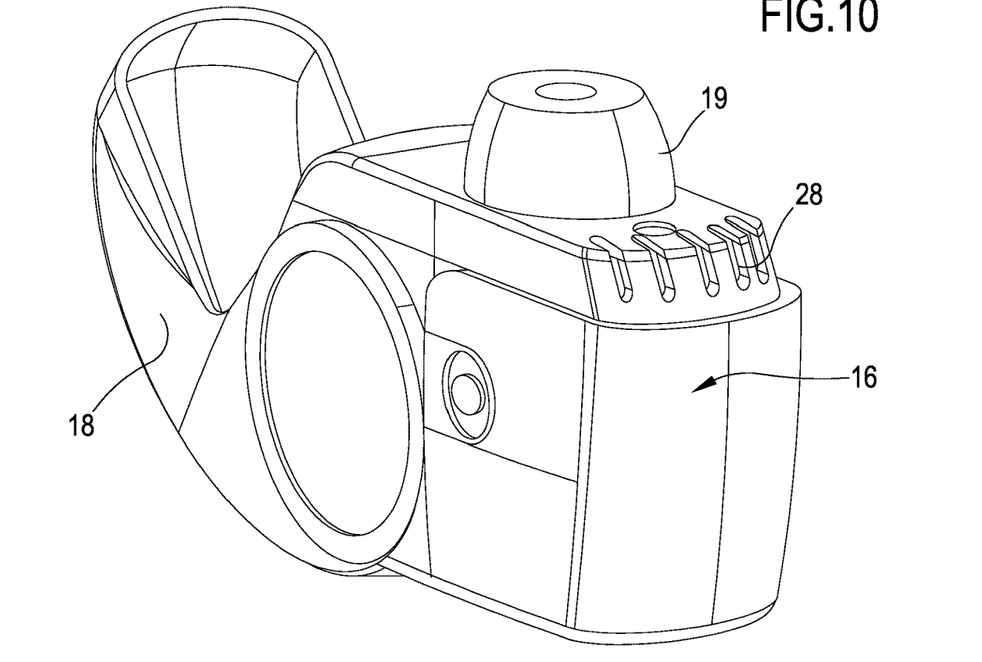
FIG. 10 shows a perspective view of a dry powder inhaler of the portion of FIG. 2.
Figure 11:
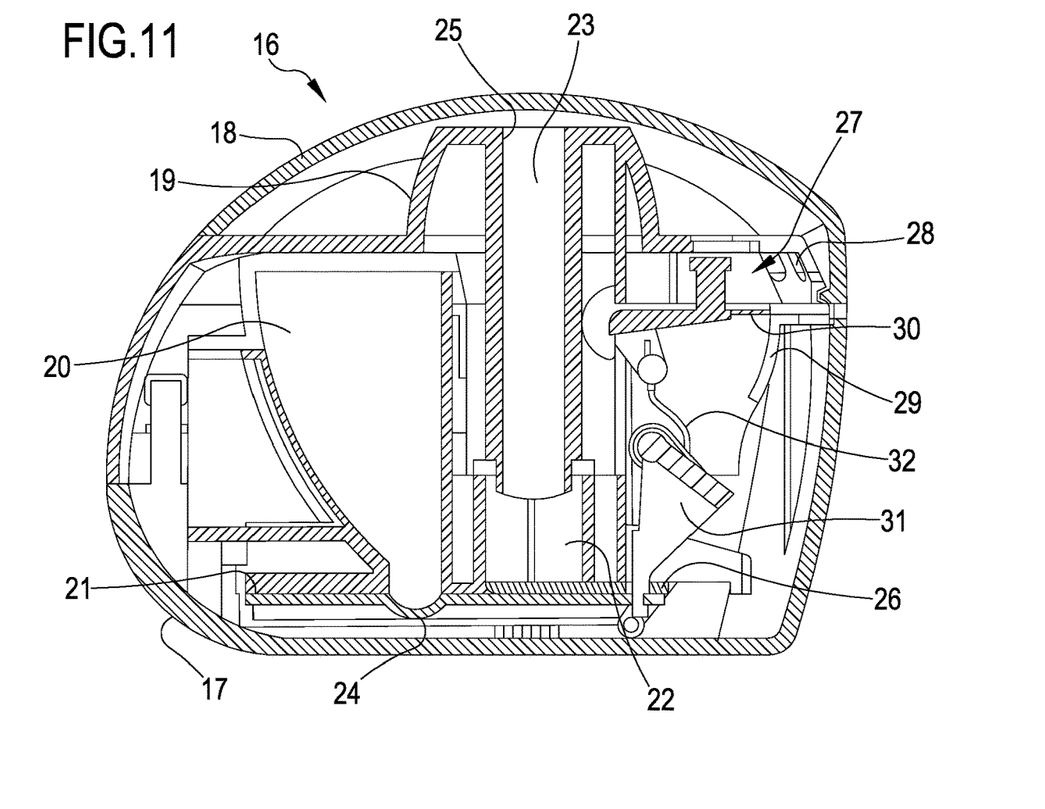
FIG. 11 is a section view of the dry powder inhaler of FIG. 10.

As shown in FIGS. 10 and 11, the dry powder inhaler 16 comprises a casing 17 with an integral cover or lid 18 which is pivotably or rotatably coupled to the casing 17. The cover 18 can be opened to reveal a mouthpiece 19 with which a user can inhale a powdered drug/medicament. The mouthpiece 19 protrudes from the casing 17.

The dry powder inhaler 16 comprises a dosing sub-assembly comprising a container or reservoir 20 for storing the powdered drug/medicament, a metering member 21 and a de-agglomerator arrangement 22 to be coupled to an inhalation channel 23 of the mouthpiece 3. The reservoir 20 is pre-loaded with a quantity of powdered drug/medicament sufficient for multiple doses. The de-agglomerator arrangement 22 is constructed such that it generates a cyclonic airflow resulting in a strong velocity gradient.

The metering member 21 is moveable between a filling position, in which a dosing recess 24 of the metering member 21 is in alignment with an opening of the container 20, so as to be filled with a dose of the powdered drug/medicament, and an inhalation position, in which the dosing recess 24 is in alignment with the inhalation channel 23 and with an outlet port 25 delimited by the mouthpiece 19. The outlet port 25 is in communication with the inhalation channel 23 for enabling inhalation of the dose of the powdered drug/medicament contained in the dosing recess 24 of the metering member 21 when the metering member 21 is in the inhalation position.

The metering member 21 is coupled to the cover 18 by a coupling mechanism, e.g., a coupling mechanism comprising profiled cam tracks, which is constructed such that opening the cover 18 causes the metering member 21 to move forward from its filling position to its inhalation position. Likewise, closing of the cover 18 causes the metering member 21 to move from its inhalation position backward to its filling position.

During the movement of the metering member 21 from the filling position to the inhalation position as well as after the metering member 21 has reached its inhalation position, the dose of the powdered drug/medicament filled in the dosing recess 24 is prevented from falling out by the protective member 26. The protective member 26 is slidable on the metering member 21 between its closed position, in which is covers the dosing recess 24, and its open position, in which it exposes the dosing recess 24 to the de-agglomerator arrangement 22 and the inhalation channel 23 when the metering member 21 is in the inhalation position.

The dry powder inhaler 16 comprises an inhalation or breath actuated mechanism 27 which is coupled to a protective member 26 for the dosing recess of the metering member 21 such that, if the protective member 26 is in a closed position in which it at least partly covers the dosing recess 24, the inhalation actuated mechanism 27 causes the protective member 26 to move to an open position, in which the protective member 26 does not cover the dosing recess 24, if an inhalation suction force on the inhalation channel exceeds a predetermined value.

The protective member 26 is held in its closed position by the above-mentioned inhalation or breath actuated mechanism 27 which is constructed such that the protective member 26 is moved from its closed position to its open position only if the inhalation suction force effected by the user in the inhalation channel 23 exceeds a predetermined level.

Furthermore, the inhalation actuated mechanism 27 is constructed such that only an inhalation suction breath, and not a blowing breath, can actuate the mechanism and can cause a movement of the protective member 26 from its closed position to its open position.

At the upper front side of the mouthpiece 19, an inlet port 28, shaped like slots, is formed which allow air inlet. The outlet port 25 and the air inlet port 28 of the dry powder inhaler 16 are placed on a same side of said dry powder inhaler 16.

The cover 18 can be rotated between a first closed configuration, in which said cover 18 is positioned on the outlet port 25 and on the air inlet port 28, and an open configuration, in which said cover 18 is spaced from the outlet port 25 and the air inlet port 28.

The inhalation actuated mechanism 27 comprises a sub-frame 29 which is shown in FIG. 11 only and holds a flap 30 acting as an inhalation actuated member, a coupling member 31, preferably in the form of a yoke, and a resilient member 32, preferably in the form of a drive spring.

When the flap 30 is held by the resilient member 32 in the horizontal position shown in FIG. 11, the protective member 26 prevents the powdered drug/medicament contained in the dosing recess 24 from being displaced from the de-agglomerator arrangement 22 if the user blows into the mouthpiece 19. Furthermore, the flap 30 provides a resistance if the user blows into the device giving positive feedback.

If, however, the metering member 21 is pushed forward by opening the cover 18, the resilient member 32 is compressed and charged, and the reset force exerted by the end on the flap 30 is released, so that the flap 30 can pivot or rotate from the horizontal first position into a second position that is pivoted downward relative to the horizontal first position if there is a sufficient high inhalation suction force in the inhalation channel 23.

In the latter case, the movement of the flap 30 into its second position releases an arm of the coupling member 31, which enables the resilient member 32, due to its compression, to move its second end and thus the coupling member 31 slightly upward.

By this rotational upward movement of the coupling member 31, a prolongation extending from the lower side of the coupling member 31 moves forward, thereby moving the protective member 26 from its closed position to its open position and exposing the dosing recess 24 to the inside of the de-agglomerator arrangement 22, so that the dose of the powdered drug/medicament can be inhaled through the de-agglomerator arrangement 22 and the inhalation channel 23 as well as the mouthpiece 19.

In this second working position, the powdered drug/medicament is in fluid communication with the air inlet port 28 and with the outlet port 25 for enabling flowing of air through the dry powder inhaler 16 from the air inlet port 28 to the outlet port 25 and inhalation of a dose of the powdered drug/medicament.

Figure 12:
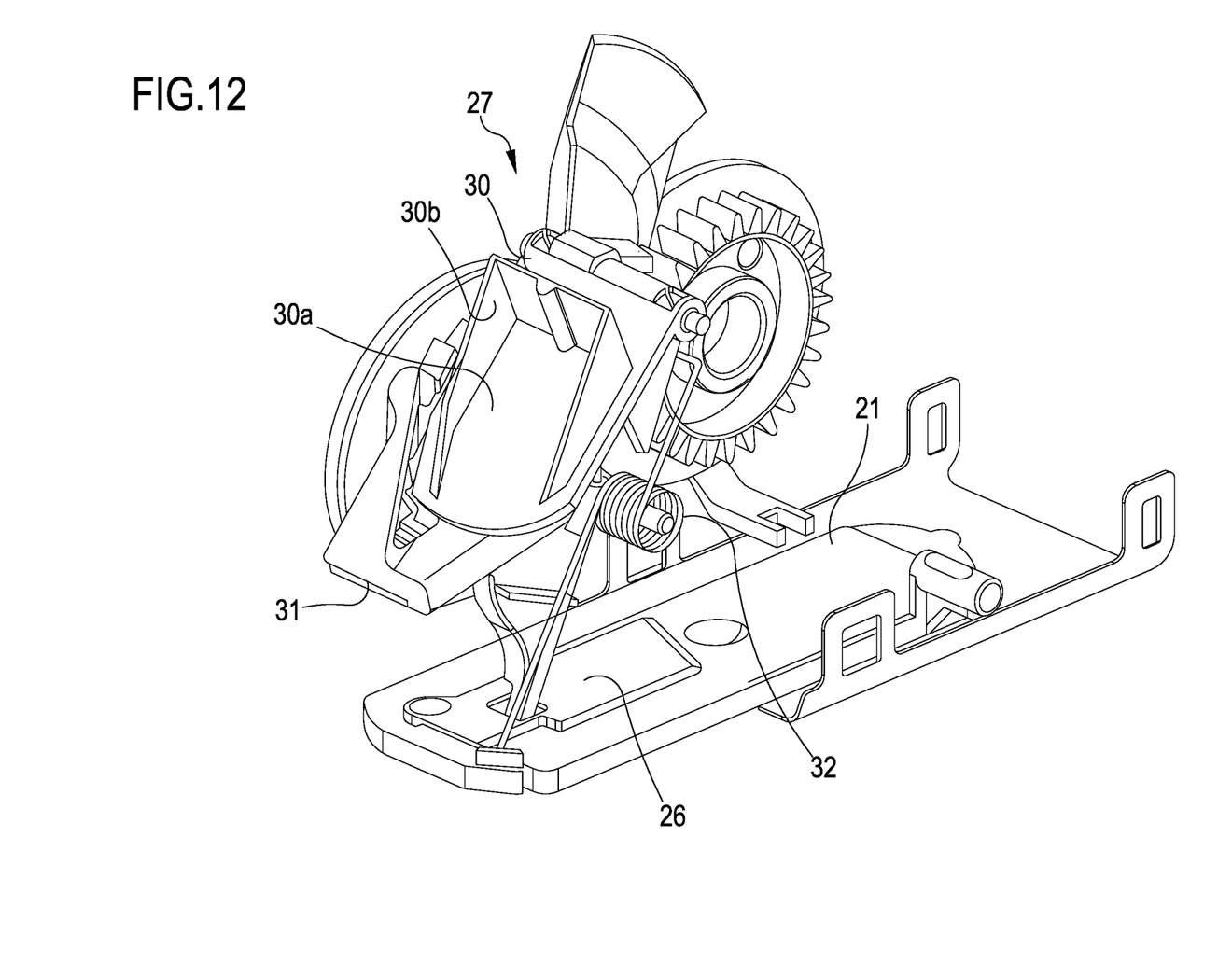
FIG. 12 shows another embodiment of the actuation mechanism of the dry powder inhaler of FIG. 10.

FIG. 12 shows a different embodiment of the inhalation actuated mechanism 27 of the dry powder inhaler 16. In this embodiment, the resilient member 32 has a similar function as the resilient member 32 shown in FIG. 11, but is different from the resilient member 32 in its shape. Therefore, as regards the functionality of the resilient member 32 of FIG. 12, in general reference can be made to the above explanations regarding the resilient member 32 shown in FIG. 11. According to the embodiment depicted in FIG. 12, the flap 30 comprises a base member 30a with a substantially plate-shaped flat portion from which a skirt 30b or frame structure projects upward. The skirt extends along the periphery of the base portion, but is open toward the front.

The coupling member 31 to be coupled to the resilient member 32 of the inhalation actuated mechanism 27 projects from the lower surface of the base portion downward. Furthermore, the base member comprises a shaft portion at a rear end of the flat portion, the shaft portion being provided to pivotably or rotatably support the flap 30 in the inhalation actuated mechanism 27 within the casing 17 of the dry powder inhaler 16.

Figure 2:
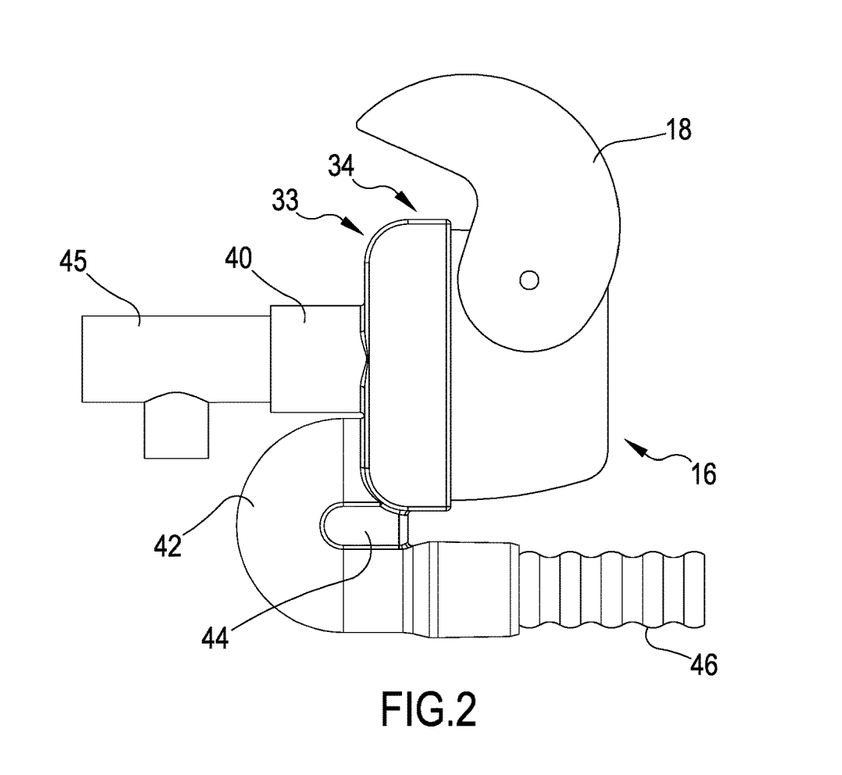
FIG. 2 shows an enlarged portion of the apparatus of FIG. 1.
Figures 3, 4, 5:
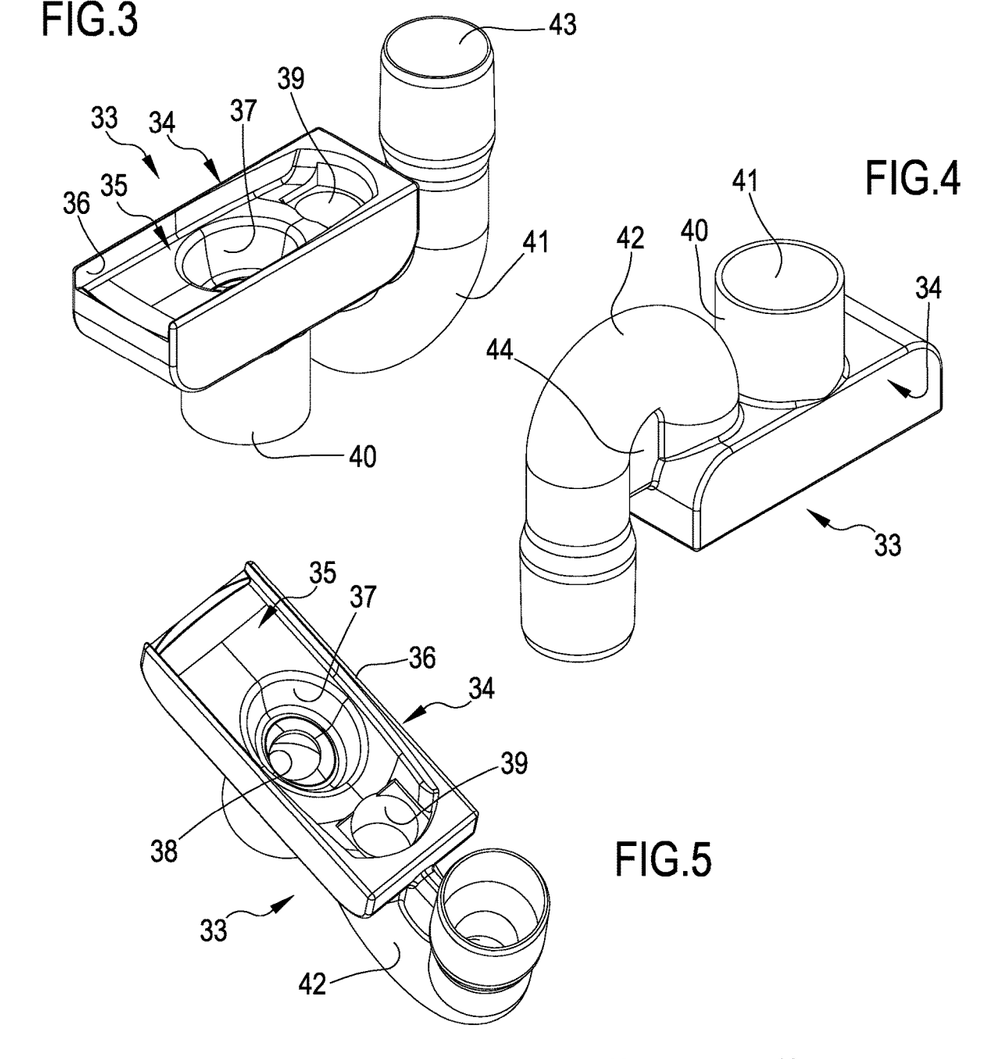
FIGS. 3 to 7 show respective views of a connector of the portion of FIG. 2.
Figure 6:
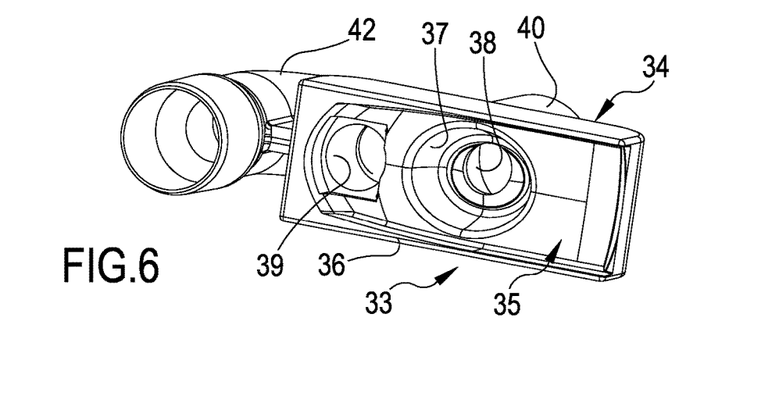
Figure 7:
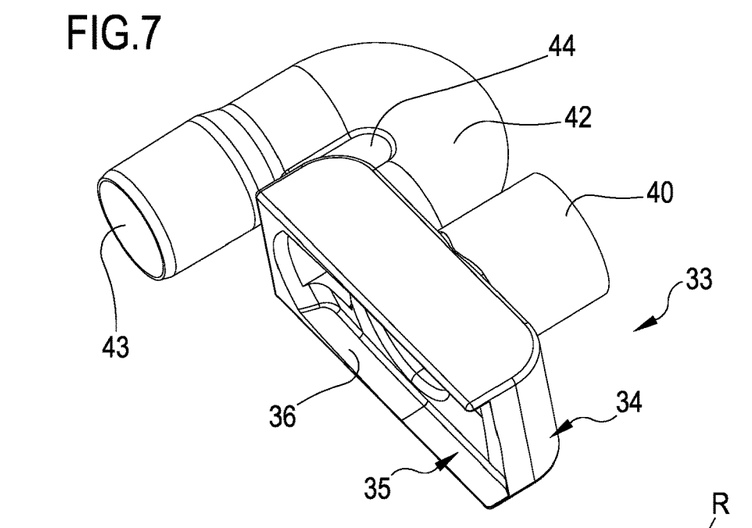

The apparatus 1 further comprises a connector or adaptor 33 connected or configured to be connected to the dry powder inhaler 16 and to the auxiliary branch 10 inspiratory line 6.

The connector 33 comprises a connector body 34 shaped like a parallelepiped. A connection seat 35 is fashioned on first face of the connector body 34. The connection seat 35 is a recess counter-shaped (shaped complementary) to the side of the dry powder inhaler 16 exhibiting the outlet port 25 and the air inlet port 28. In the illustrated embodiment, the connection seat 35 is delimited by a peripheral edge 36 configured to abut against an edge of the connector body 34. The peripheral edge 36 is interrupted on a side portion of the connector body 34 to allow to slip said connector body 34 on the dry powder inhaler 16 when the cover 18 is open (FIG. 2). In a different embodiment, the connector 33 may be snap-fitted on the dry powder inhaler 16. In both these embodiments, the connector 33 is detachably connected to the dry powder inhaler 16.

The connection seat 35 presents a recess 37 for the mouthpiece 19 of the dry powder inhaler 16. A first opening 38 is fashioned in the recess 37, passes through the connection body 34 and opens on a second face of the connection body 34 opposite the first face. A second opening 39 is fashioned in the connection seat and it is placed at a side of the recess 37. The second opening 39 passes through the connection body 34 and opens on the second face of the connection body 34 opposite the first face.

A straight tube section 40 protrudes from the second face of the connector body 34. The straight tube section 40 delimits a first duct 41. The first opening 38 is placed at a proximal end of the straight tube section 40 and the first duct 41 is in fluid communication with the first opening 38.

A curved tube 42 is connected to the connector body 34 and protrudes form the second face of said connector body 34. The curved tube 42 delimits a second duct 43. The second opening 39 is placed at a proximal end of the curved tube 42 and the second duct 43 is in fluid communication with the second opening 39.

Figure 8:
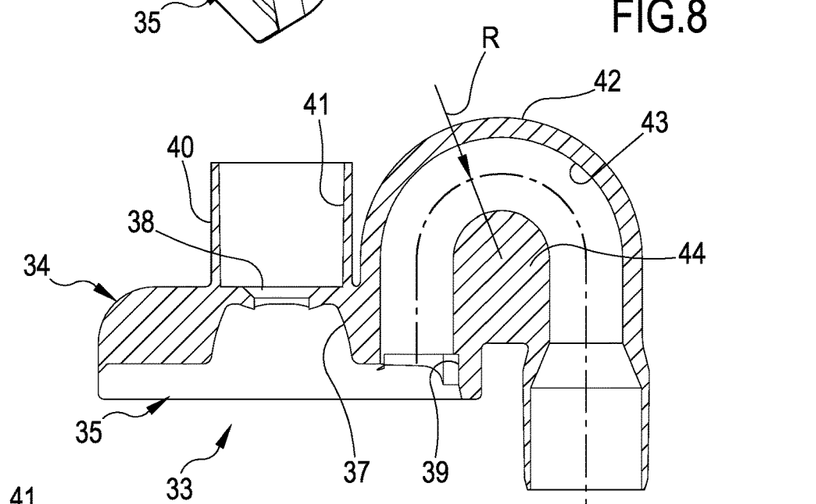
FIG. 8 is a section view of the connector of FIGS. 3 to 7.
Figure 9:
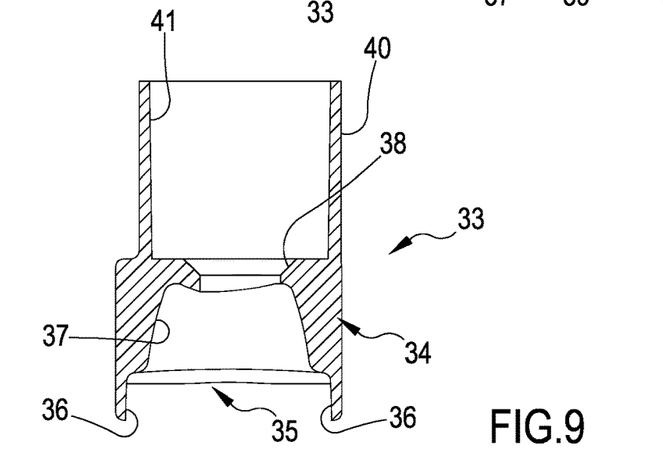
FIG. 9 is another section view of the connector of FIGS. 3 to 7.

As shown in FIG. 8, the proximal end of the curved tube 42 is parallel to the first duct 41 and/or to the straight tube section 40. The curved tube 42 is U-shaped and it is bent backwards with respect to the straight tube section 40 such that a terminal end of the curved tube 42 is parallel to the first duct 41 and opens on an opposite side. When the connector 33 is mounted on the dry powder inhaler 16 (FIG. 2), the terminal end of the curved tube 42 is placed at a side of the dry powder inhaler 16. A stiffening plate 44 is placed between two arms of the U-shaped curved tube 42. The connector 33 (connector body 34, straight tube section 40, curved tube 42, stiffening plate 44) is made of a single piece of molded plastic.

The first duct 41 inside the straight tube section 40 has a diameter of about 22 mm to allow insertion and blocking of a tube section end. The second duct 43 inside the curved tube 42 has a passage section of about 127 mm$^2$. The terminal end of the curved tube 42 has an inner diameter of about 19.5 mm to allow insertion and blocking of a tube section end. A curvature radius R of the curved tube 42 (curvature radius R of a mid-line of the curved tube 42 or of the second duct 43) is 15 mm. When the connector 33 is mounted on the dry powder inhaler 16, the first duct 41 faces the outlet port 25 of the dry powder inhaler 16 and the second duct 43 faces the air inlet port 28 of the dry powder inhaler 16.

As shown in FIG. 2, the connector 33 is connected to the auxiliary branch 10 of the inspiratory line 6 by connecting a tube section 45 of said inspiratory line 6 placed downstream the dry powder inhaler 16 to the straight tube section 40 and by connecting a tube section 46 of the inspiratory line 6 placed upstream the dry powder inhaler 16 to the curved tube 42.

The ventilation circuit 3 further comprises at least one valve disposed upstream the dry powder inhaler 16 to selectively direct ventilation air generated by the ventilator 2 through the main branch 9 or through the auxiliary branch 10. In the disclosed embodiment, the ventilation circuit 3 comprises a first valve 47 on the main branch 9 and a second valve 48 on the auxiliary branch 10.

The first valve 47 and the second valve 48 may be operatively connected to the electronic control unit to automatically control said valves 47, 48.

A non-return/one-way valve 49 is disposed on the tube section 45 and downstream the dry powder inhaler 16 to prevent air from flowing back into the dry powder inhaler 16. The non-return valve 49 is placed between the second junction 13 and the third junction 14.

A filter 50 is placed in line on the auxiliary branch 10 and upstream the dry powder inhaler 16 for drying the air flow before it comes in contact with the drug/medicament.

In use and according to the method of the present invention, after associating the artificial airway to the patient P and to the ventilator through the ventilation circuit, mechanical ventilation is started.

The second valve 48 on the auxiliary branch 10 is closed and the first valve 47 on the main branch 9 is open to allow ventilation.

The cover 18 of the dry powder inhaler 16 is opened and the connector 33 is mounted on the on the dry powder inhaler 16 as disclosed in the previous passages. Since the cover is open, the metering member 21 is pushed forward and the flap 30 can rotate from the horizontal first position into the second position that is pivoted downward relative to the horizontal first position if there is a sufficient differential pressure between the air inlet port 28 and outlet port 25.

The connector 33 is connected to the tube section 45 placed downstream the dry powder inhaler 16 and to the tube section 46 placed upstream the dry powder inhaler 16.

When a dose of drug/medicament is to be delivered from the dry powder inhaler 16 and administered to the patient P, the first valve 47 is closed and the second valve 48 is open. The pressure of ventilation air generated by the ventilator 2 triggers the dry powder inhaler 16 to deliver a dose during inspiration cycle of the mechanical ventilator 2. Such pressure moves the flap 30 to the second position. In this position, the powdered drug/medicament is in fluid communication with the air inlet port 28 and with the outlet port 25. The flow of air through the dry powder inhaler 16 from the air inlet port 28 to the outlet port 25 during inspiration cycle delivers a dose of the powdered drug/medicament to the patient P. Dose delivery is performed during mechanical ventilation and it is generated by mechanical ventilation.

Any ventilator system commercially available could advantageously be used, for example the Monnal T75, available from Air Liquid Medical Systems S.p.A (Bovezzo, Italy).

Typically, the following ventilation conditions are set-up: tidal volume: 400-500 ml; PEEP 5-20 cmH$_2$O; Flow rate: about 40-45 l/min; breath frequency: 15 bpm; Inspiration Expiration Ratio (IER) from 1:25 to 1:4.

In other embodiments, not shown, the connector 33 and the dry powder inhaler 16 may be integrally joined.

In other embodiments, not shown, the casing of the dry powder inhaler 16 is shaped to include the first duct 41 and the second duct 43.

In other embodiments, the dry powder inhaler may be a single dose dry powder inhaler or a multi-dose dry powder inhaler with pre-subdivided single doses.

The invention is illustrated by the following Example.

Example

A powder formulation was prepared according to the teaching of Examples 2 and 3 of WO 2013/110632 and loaded in the multi-dose dry powder inhaler described in WO 2016/000983.

A ventilator system Monnal T75, available from Air Liquid Medical Systems S.p.A (Bovezzo, Italy) was used.

A Catheter mounth (ID 10 mm, length 17 cm) and an endotracheal catheter (ID 8 mm, length 8.5 cm) were also utilized.

Other equipments were standard.

The following conditions were set-up: tidal volume: 500 ml; PEEP 5 cmH$_2$O; Flow rate: about 41 l/min; breath frequency: 15 bpm.

All tests were performed at room temperature and lung temperature (about 37° C.) with in line humidification (about 75% relative humidity system).

The inhaler was connected to the ventilation system through the connector of the invention.

The evaluation of the aerosol performance was carried out using the Next Generation Impactor (NGI) according to the conditions reported in the European Pharmacopeia 8.5th Ed 2015, par 2.9.18, pages 309-320.

After aerosolization of three doses from the inhaler device, the NGI apparatus was disassembled and the amounts of drug deposited in the stages were recovered by washing with a solvent mixture and then quantified by High-Performance Liquid Chromatography (HPLC). The following drugs were determined: formoterol fumarate dihydrate (FF) and beclometasone dipropionate (BDP).

The following parameters, were calculated: i) the delivered dose which is the amount of drug delivered from the device recovered in the all parts of impactor; ii) the fine particle mass (FPM) which is the amount of delivered dose having a particle size equal to or lower than 5.0 micron; iii) the extrafine FPM which is the amount of delivered dose having a particle size equal to or lower than 2.0 micron and/or equal to or lower than 1.0 micron and; iv) the fine particle fraction (FPF) which is the ratio between the fine particle mass and the delivered dose; v) the extrafine particle fraction which is the ratio between the extrafine FPM and the delivered dose; vi) the MMAD.

The results (mean value±S. D) are reported in Table 1.

TABLE 1

| | FPM (µg) | FPF (% on DD) | EFPM (µg) | EFPF (% on DD) | DD (µg) | MMAD (µg) |
|---|---|---|---|---|---|---|
| BDP + FF 100 + 6 µg/10 mg DPI - Release | | | | | | |
| FF | 2.88 | 62.09 | 0.88 | 18.98 | 4.64 | 1.68 |
| BDP | 51.99 | 64.14 | 23.85 | 29.43 | 81.05 | 1.32 |
| BDP + FF 100 + 6 µg/10 mg DPI 37° C. 75% RH T- vol 500 | | | | | | |
| FF | 2.27 | 59.19 | 1.06 | 27.69 | 3.84 | 1.08 |
| BDP | 41.19 | 61.92 | 23.12 | 34.76 | 66.52 | 0.85 |

As it can be appreciated, upon connection to the ventilation system through the connector of the invention, the aerosol performances are comparable with those from the DPI inhaler at the release.

In particular, the extrafine particle fraction turned out to be higher than 20%.

The invention claimed is:

1. An apparatus to administer drugs to mechanically ventilated patients, the apparatus comprising:
- a mechanical ventilator;
- an artificial airway configured to be associated with a patient;
- a ventilation circuit connecting the mechanical ventilator to the artificial airway;

wherein the ventilation circuit comprises:
- an inspiratory line;
- a dry powder inhaler disposed in line on the inspiratory line;
- a connector operatively connected to the dry powder inhaler and to the inspiratory line;

wherein the connector comprises:
- a connector body;
- a first duct facing an outlet port of the dry powder inhaler and connected or configured to be connected to a first tube section of the inspiratory line placed downstream the dry powder inhaler;
- a second duct facing an air inlet port of the dry powder inhaler and connected or configured to be connected to a second tube section of the inspiratory line placed upstream the dry powder inhaler; and
- wherein the first duct and the second duct of the connector present respectively a first opening and a second opening placed side by side on the connector body.

2. The apparatus according to claim 1, wherein the outlet port and the air inlet port of the dry powder inhaler are placed on a same side of said dry powder inhaler.

3. The apparatus according to claim 1, wherein the connector comprises a curved tube connected to the connector body; said curved tube delimiting at least in part the second duct.

4. The apparatus according to claim 3, wherein the connector comprises a straight tube section protruding from the connector body, wherein said straight tube section delimits at least in part the first duct; wherein the curved tube is bent backwards with respect to the straight tube section.

5. The apparatus according to claim 3, wherein the curved tube presents a terminal end substantially parallel to the first duct.

6. The apparatus according to claim 3, wherein the curved tube is in part placed at a side of the dry powder inhaler.

7. The apparatus according to claim 3, wherein a curvature radius of the curved tube is between 14 mm and 16 mm.

8. The apparatus according to claim 3, wherein the curved tube is U-shaped.

9. The apparatus according to claim 3, wherein the second duct inside the curved tube presents a passage section between 120 $mm^2$ and 130 $mm^2$.

10. The apparatus according to claim 1, wherein the connector is detachably connected to the dry powder inhaler.

11. The apparatus according to claim 2, wherein the connector has a connection seat counter-shaped to the side of the dry powder inhaler exhibiting the outlet port and the air inlet port; wherein the first opening and the second opening open in said connection seat.

12. The apparatus according to claim 1, wherein the inspiratory line comprises a main branch and an auxiliary branch disposed in parallel; wherein the dry powder inhaler is placed on the auxiliary branch; wherein the ventilation circuit comprises at least one valve disposed upstream the dry powder inhaler to selectively direct ventilation air through the main branch or through the auxiliary branch; wherein the ventilation circuit further comprises an expiratory line connecting the artificial airway to the mechanical ventilator.

13. The apparatus according to claim 12, wherein, when said at least one valve, is configured to direct ventilation air through the auxiliary branch, pressure of ventilation air triggers the dry powder inhaler to deliver a dose.

14. The apparatus according to claim 1, wherein the dry powder inhaler is a medium-high resistance dry powder inhaler; wherein the dry powder inhaler is a multi-dose dry powder inhaler.

* * * * *